United States Patent [19]

Girard et al.

[11] Patent Number: 5,350,744
[45] Date of Patent: Sep. 27, 1994

[54] PHENYLNAPHTHALENE LACTONES AS INHIBITORS OF LEUKOTRIENE BIOSYNTHESIS

[75] Inventors: Yves Girard, Ile Bizard; Pierre Hamel, Vimont, both of Canada

[73] Assignee: Merck Frosst Canada, Inc., Quebec, Canada

[21] Appl. No.: 937,078

[22] Filed: Aug. 27, 1992

[51] Int. Cl.$^5$ .................. A61K 31/655; A61K 31/44; C07D 405/12

[52] U.S. Cl. .................. 514/149; 514/278; 514/316; 514/318; 514/337; 514/826; 514/912; 546/15; 546/187; 546/193; 546/194; 546/269

[58] Field of Search .............. 546/269, 15, 187, 193, 546/194; 514/337, 826, 912, 149, 278, 316, 318

[56] References Cited

U.S. PATENT DOCUMENTS

| | | | |
|---|---|---|---|
| 4,486,445 | 12/1984 | Patel et al. | 549/299 |
| 4,937,373 | 6/1990 | Carson et al. | 514/545 |

FOREIGN PATENT DOCUMENTS

| | | |
|---|---|---|
| 0188248 | 7/1986 | European Pat. Off. |
| 0351194 | 1/1990 | European Pat. Off. |
| 0372385 | 6/1990 | European Pat. Off. |
| 0375368 | 6/1990 | European Pat. Off. |
| 0375404 | 6/1990 | European Pat. Off. |
| 0375452 | 6/1990 | European Pat. Off. |
| 0380982 | 8/1990 | European Pat. Off. |
| 0381375 | 8/1990 | European Pat. Off. |
| 0385662 | 9/1990 | European Pat. Off. |
| 0385663 | 9/1990 | European Pat. Off. |
| 0385679 | 9/1990 | European Pat. Off. |
| 0385680 | 9/1990 | European Pat. Off. |
| 0409413 | 1/1991 | European Pat. Off. |
| 0462812 | 12/1991 | European Pat. Off. |
| 0462830 | 12/1991 | European Pat. Off. |

Primary Examiner—C. Warren Ivy
Assistant Examiner—A. A. Owens
Attorney, Agent, or Firm—Mollie M. Yang; David L. Rose

[57] ABSTRACT

Compounds having the formula I:

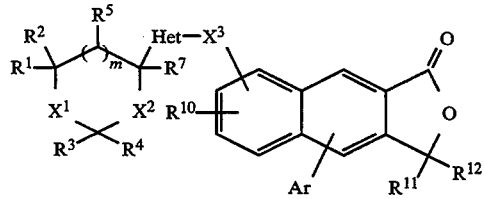

are inhibitors of leukotriene biosynthesis. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection and in preventing the formation of atherosclerotic plaques.

13 Claims, No Drawings

PHENYLNAPHTHALENE LACTONES AS INHIBITORS OF LEUKOTRIENE BIOSYNTHESIS

CROSS-REFERENCE

The hydroxyacid forms of the present lactones are the subject of a co-pending U.S. patent application, attorney docket no. 18812, Ser. No. 07/936,811, filed on even date herewith, which is incorporated herein by reference.

BACKGROUND OF THE INVENTION

The leukotrienes constitute a group of locally acting hormones, produced in living systems from arachidonic acid. The major leukotrienes are Leukotriene $B_4$ (abbreviated at $LTB_4$), $LTC_4$, $LTD_4$, and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

European patent application 375,404 (Jun. 27, 1990) describes certain naphthalene-containing heterocyclic ethers of structure A which are inhibitors of the enzyme 5-lipoxygenase. EP application 375,452 (Jun. 27, 1990) describes naphthalene-containing hydrocarbon ethers of structure B which are reported to possess the same activity. EP application 462,830 (Dec. 27, 1991) describes bicyclic heterocycle-containing hydrocarbon ethers of structure C which are reported to possess the same activity. All these series of prior art compounds differ significantly from the present invention in that they lack both the aryl substituent and the additional fused ring of the present compounds.

A series of natural products known as the justicidins are referred to in the Merck Index, 11th edition, 1989, no. 5154. The justicidins differ considerably from the present compounds in that they are lacking the large Het group.

Hence the compounds of the present invention are completely novel and unexpectedly have biological activity as leukotriene biosynthesis inhibitors.

$$Ar^1-A^1-O-Ar^2-\underset{\underset{R^3}{|}}{\overset{\overset{OR^1}{|}}{C}}-R^2 \qquad \underline{A} \text{ EP 375,404 ICI-Pharm a}$$

$$Ar^1-A^1-O-Ar^2-\underset{\underset{R^3}{|}}{\overset{\overset{OR^1}{|}}{C}}-R^2 \qquad \underline{B} \text{ EP 375,452 ICI-Pharm a}$$

$$Ar^1-A^1-O-Ar^2-\underset{\underset{R^3}{|}}{\overset{\overset{R^1}{|}}{C}}-R^2 \qquad \underline{C} \text{ EP 462,830 ICI-Pharm a}$$

-continued

Justicidins, Merck Index No. 5154

SUMMARY OF THE INVENTION

The present invention relates to phenylnaphthalene lactones having activity as leukotriene biosynthesis inhibitors, to methods for their preparation, and to methods and pharmaceutical formulations for using these compounds in mammals (especially humans).

Because of their activity as leukotriene biosynthesis inhibitors, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection and in preventing the formation of atherosclerotic plaques.

DETAILED DESCRIPTION OF THE INVENTION

The compounds of the present invention may be represented by the following formula I:

wherein:
$R^1$, $R^5$, and $R^{11}$ is each independently H, OH, lower alkyl, or lower alkoxy;
$R^2$ is H, lower alkyl, or together with $R^1$ forms a double bonded oxygen (=O);
$R^3$ is H, lower alkyl, hydroxy lower alkyl, lower alkoxy lower alkyl, or is joined to $R^1$ to form a carbon bridge of 2 or 3 carbon atoms or a mono-oxa carbon bridge of 1 or 2 carbon atoms, said bridge optionally containing a double bond;
$R^4$, $R^{12}$, and $R^{14}$ is each independently H or lower alkyl;
$R^6$ is H or lower alkyl, or two $R^6$ groups on the same or adjacent carbons can form a saturated ring of 3 to 8 members;
$R^7$ is H, OH, lower alkyl, lower alkoxy, lower alkylthio, or lower alkylcarbonyloxy;
$R^8$ is H, halogen, lower alkyl, lower alkoxy, $CF_3$, CN, $COR^{14}$ or a non-bonded electron pair;
$R^9$ and $R^{10}$ is each independently H, lower alkyl, lower alkoxy, hydroxy lower alkyl, lower alkoxy lower alkyl, lower alkylthio lower alkyl, lower alkylthio lower alkylcarbonyl, $(R^8)_2$-phenylthio lower alkyl, halogen, CN, $NO_2$, $CF_3$, $N_3$, $N(R^{13})_2$, $NR^{13}COR^{14}$, $NR^{13}CON(R^{13})_2$, $SR^{15}$, $S(O)R^{15}$, $S(O)_2R^{15}$, $S(O)_2N(R^{13})_2$, $COR^{14}$, $CON(R^{13})_2$, $CO_2R^{14}$, $C(R^{14})_2OC(R^{14})_2\text{-}CO_2R^{14}$, or $C(R^{14})_2CN$;

$R^{10}$ is attached to either ring of the naphthalene ring system;

$R^{13}$ is H or lower alkyl, or two $R^{13}$ groups attached to the same nitrogen may form a saturated ring of 5 or 6 members, optionally containing a second heteroatom chosen from O, S, or $NR^4$;

$R^{15}$ is lower alkyl, phenyl-$(R^8)_2$, or $CF_3$;

$X^1$ is O, S, S(O), $S(O)_2$, or $C(R^6)_2$;

$X^2$ is O, S, $C(R^6)_2$, or bond;

$X^3$ is $C(R^6)_2S$, $SC(R^6)_2$, $C(R^6)_2O$, $OC(R^6)_2$, $CR^6=CR^6$, $C(R^6)_2C(R^6)_2$, O, or S;

Ar is phenyl$(R^9)_2$ or naphthyl$(R^9)_2$;

Het is arylene-$(R^8)_2$, wherein arylene is a 5-membered aromatic ring wherein one carbon atom is replaced by O or S and 0–2 carbon atoms are replaced by N; a 5-membered aromatic ring where 1–3 carbon atoms are replaced by N; a 6-membered aromatic ring wherein 1–3 carbon atoms are replaced by N; 2- or 4-pyranone; or 2- or 4-pyridinone;

m is 0 or 1 or a pharmaceutically acceptable salt thereof.

The compounds of Formula I are preferably administered in the hydroxyacid form, which can be prepared by treating the lactones herein by methods known in the art such as with a strong base. Discussions herein of dosages, compositions, combinations with other drugs, etc. can be applied to said hydroxyacid form.

A preferred embodiment of the present invention is represented by Formula Ia:

wherein the substituents are as defined for Formula I, or a pharmaceutically acceptable salt thereof.

Another embodiment of the present invention is represented by Formula Ib wherein:

$R^1$ is H, Me, or OMe;

$R^3$ is H or Me;

$R^1$ and $R^3$ together are —CH=CH—, —CH$_2$CH$_2$—, —OCH$_2$—, or —CH$_2$O—;

$R^7$ is OH or OMe; and

Het is 5,3-Pye; 6,2-Pye; 4,2-Pye; or 2,4-Pye;

or a pharmaceutically acceptable salt thereof,

Definitions

The following abbreviations have the indicated meanings:

Ac=acetyl
Bn=benzyl
c-Bu=cyclobutyl
c-Pen=cyclopentyl
c-Pr=cyclopropyl
c-Hex=cyclohexyl
i-Pr=isopropyl
n-Pt=normal propyl
n-Bu=normal butyl
i-Bu=isobutyl
s-Bu=secondary butyl
t-Bu=tertiary butyl
Et=ethyl
Me=methyl
Ph=phenyl
Pye=pyridindiyl
Thi=thiophendiyl
$C_3H_5$=allyl Alkyl is intended to include linear and branched structures and combinations thereof.

The term "alkyl" includes "lower alkyl" and extends to cover carbon fragments having up to 20 carbon atoms. Examples of alkyl groups include octyl, nonyl, undecyl, dodecyl, tridecyl, tetradecyl, pentadecyl, eicosyl, 3,7-diethyl-2,2-dimethyl-4-propylnonyl, and the like.

"Lower alkyl" means alkyl groups of from 1 to 7 carbon atoms. Examples of lower alkyl groups include methyl, ethyl, propyl, isopropyl, butyl, s- and t-butyl, pentyl, hexyl, heptyl, and the like.

"Lower alkoxy" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

"Hydroxy lower alkyl" means a lower alkyl group carrying a hydroxy group; e.g. —$CH_2C$-$H(OH)CH_2CH_3$.

"Lower alkoxy lower alkyl" means a lower alkyl group carrying a lower alkoxy group; e.g. —$CH_2C$-$H_2OCH_3$.

"Lower alkylthio" means alkylthio groups of from 1 to 7 carbon atoms of a straight, branched, or cyclic configuration. Examples of lower alkylthio groups include methylthio, ethylthio, isopropylthio, cyclobutylthio, and the like.

"Lower alkylcarbonyl" means alkylcarbonyl groups of from 1 to 8 carbon atoms of a straight, branched, or cyclic configuration. Examples of lower alkylcarbonyl groups are formyl, 2-methylbutanoyl, cyclohexylacetyl, etc. By way of illustration, the 2-methylbutanoyl group signifies —$COCH(CH_3)CH_2CH_3$.

Examples of "arylene" are furan, thiophene, isoxazole, isothiazole, oxazole, thiazole, 1,3,4-oxadiazole, 1,3,4-thiadiazole, 1,2,5-oxadiazole, 1,2,5-thiaziazole, pyrrole, pyrazole, imidazole, 1,3,4-triazole, pyridine, pyrazine, pyrimidine, pyridazine, 1,2,3-triazine, 1,2,4-triazine, 1,3,5-triazine, and the like.

Halogen includes F, Cl, Br, and I.

It is intended that the definitions of any substituent (e.g., $R^4$ $R^8$, etc.) in a particular molecule be independent of its definitions elsewhere in the molecule. Thus, —$C(R^6)_2O$— represents —$CHCH_3O$—, —$C(CH_3)_2O$—, etc.

Optical Isomers—Diastereomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzene-sulfonic, benzoic, camphorsulfonic, citric, ethane-sulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

Utilities

The ability of the compounds of Formula I to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as psoriasis, atopic eczema, and the like, 6) cardiovascular disorders such as angina, formation of atherosclerotic plaques, myocardial ischemia, hypertension, platelet aggregation, and the like, 7) renal insufficiency arising from ischaemia induced by immunological or chemical (cyclosporin) etiology, 8) migraine or cluster headache, 9) ocular conditions such as uveitis, 10) hepatitis resulting from chemical, immunological, or infectious stimuli, 11) trauma or shock states such as burn injuries, endotoxemia, and the like, 12) allograft rejection, 13) prevention of side effects associated with therapeutic administration of cytokines such as Interleukin II and tumor necrosis factor, 14) chronic lung diseases such as cystic fibrosis, bronchitis, and other small- and large-airway diseases, 15) cholecystitis, and 16) multiple sclerosis.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol- induced renal failure. The compounds also act as inhibitors of tumor metastasis and exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Pharmaceutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and. optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200, and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

Combinations With Other drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the oxicams; and
(5) the biphenylcarboxylic acid derivatives; or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

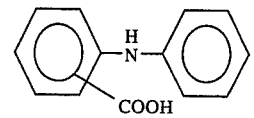

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

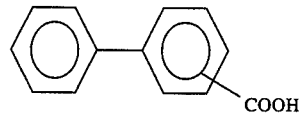

which can bear a variety of substituents and in which the free —COOH group can be in the form of a pharmaceutically acceptable salt group, e.g., —COO$^-$Na$^+$.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

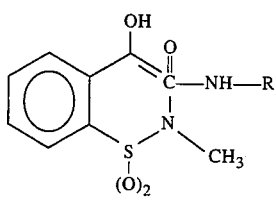

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate.

The following NSAIDs, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$- or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxy-propane and related compounds described in British Patent Specifications 1,144,905 and 1,144,906. Another useful pharmaceutical composition comprises the Formula I compounds in combination with serotonin antagonists such as methysergide, the serotonin antagonists described in Nature, Vol. 316, pages 126–131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Methods of Synthesis

Compounds of the present invention can be prepared according to the following methods. The substituents are the same as in Formula I except where defined otherwise.

Scheme I

The route which is used to prepare the lactone VI is outlined in Scheme I. The aryl carboxaldehyde II is converted to the thioacetal III by treatment with thiophenol in the presence of a Lewis-Acid such as $BF_3 \cdot Et_2O$ in an organic solvent such as isopropyl acetate. The thioacetal III is then converted to the lactone V by treatment with a base such as n-BuLi in an organic solvent such as THF followed by the successive additions of 2-(5H) furanone and the benzyloxyaryl carboxaldehyde IV in an organic solvent such as THF and after quenching with an acid such as HOAc. The cyclization, dehydration and debenzylation are achieved simultaneously by heating the lactone V in the presence of an acid such as TFA, and using thioanisole as organic solvent providing the lactone VI.

Scheme II

The preparation of compounds of Formula I (wherein $X^3 = -C(R^6)_2O-$) is described in Scheme II. A first method requires coupling of the naphthol VI with a benzylic halide or activated alcohol of type VII (wherein X=Cl, Br, I, OMs, OTs) in a polar organic solvent such DMF in the presence of an inorganic base such as $Cs_2CO_3$.

In an alternate procedure, the naphthol VI is condensed with the heterocyclic alcohol VII (wherein X=OH) in the presence of a phosphine such as $Ph_3P$ and a azodicarboxylate diester, in a solvent such as THF, to afford Formula I (wherein $X^3 = -C(R^6)_2O-$) compounds.

Scheme III

The synthesis of compounds of Formula I (wherein $X^3 = -OCH_2-$) is described in Scheme III. The phenol lactone VI may be converted to the triflate VIII by treatment with trifluoromethanesulfonic anhydride in the presence of an organic base such as pyridine in a solvent such as $CH_2Cl_2$. Subsequent treatment of VIII in a solvent such as DMSO/MeOH with an organic base such as triethylamine, a phosphine such as 1,1'-bis(-diphenylphosphino)-ferrocene, a palladium(II) salt such as palladium-(II)acetate under an atmosphere of carbon monoxide will lead to the ester IX. The hydrolysis of the ester IX may be achieved using an inorganic base such as lithium hydroxide in water and the resulting acid may be reduced to the alcohol XI by treatment with a chloroformate such as isopropyl chloroformate in the presence of an organic base such as triethylamine in an organic solvent such as THF, followed by addition of a reducing agent such as sodium borohydride in water. The alcohol XI may be then converted to the halide XII by treatment with triphenylphosphine, imidazole and $CBr_4$ in an organic solvent such as $CH_2Cl_2$. Coupling of halide XII with the appropriate phenol XIII in an organic solvent such as DMF using an inorganic base such as $K_2CO_3$ provides compounds of formula I (wherein $X^3 = -OCH_2-$) of the present invention.

Scheme IV

Scheme IV illustrates the conversion of compounds of formula I (wherein $R^{11}/R^{12}=H$) to formula I (wherein $R^{11}/R^{12}$ is not H). Compounds of formula I (wherein $R^{11}/R^{12}=H$) may be alkylated by treatment with an organic base such as lithium diisopropylamide in an organic solvent such as THF, followed by quenching with an alkyl halide such as methyl iodide. A second alkylation may be achieved by using the same conditions. Conversion of compounds of formula I (wherein $R^{11}/R^{12}=H$) to compounds I (wherein $R^{11}=OH$, $R^{12}=H$) may be achieved by an hydrolysis process using an inorganic base such as NaOH in a solvent such as $EtOH/H_2O$ to provide the carboxylate salt XIV, followed by an oxidation step using an oxidizing agent such as pyridinium chlorochromate in an organic solvent such as $CH_2Cl_2$. The reaction of compound I ($R^{11}=OH$, $R^{12}=H$) with a lower alkyl Grignard or lithium reagent may yield compound I ($R^{11}$=lower alkyl, $R^{12}=H$).

SCHEME I
PREPARATION OF LACTONE INTERMEDIATES

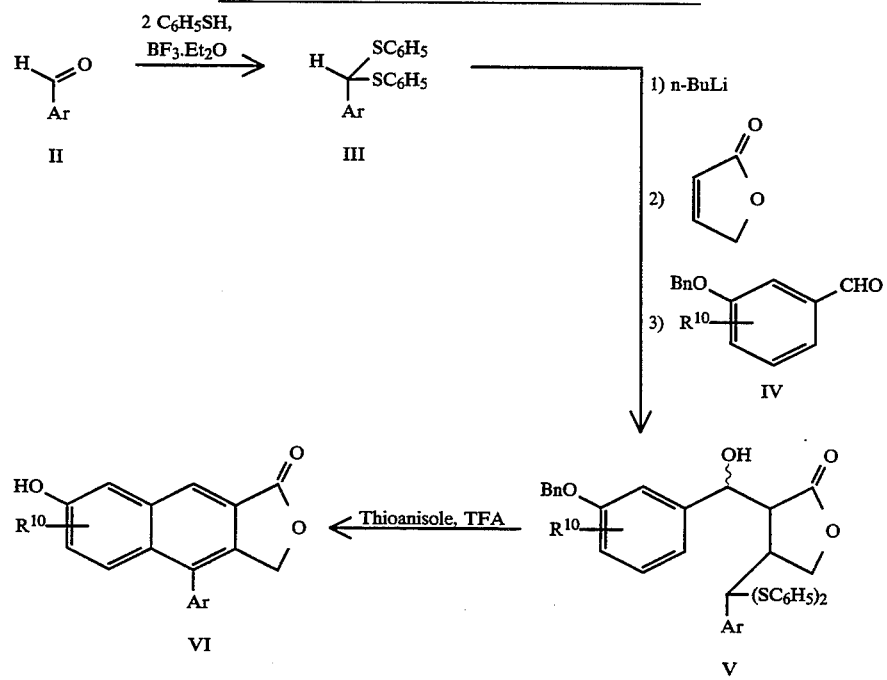

SCHEME II
PREPARATION OF FINAL PRODUCTS
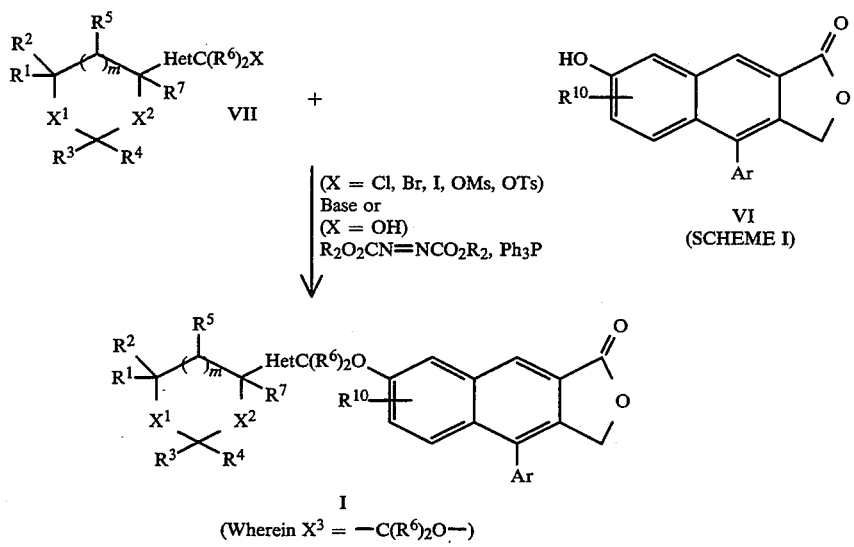
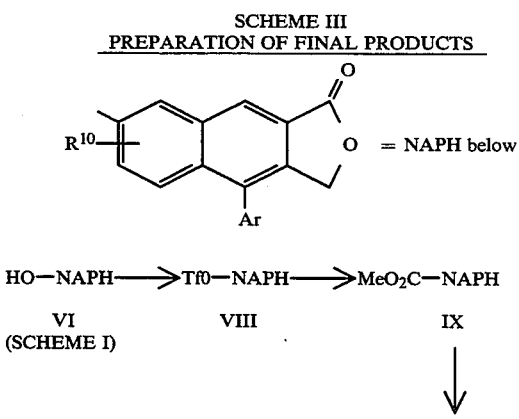
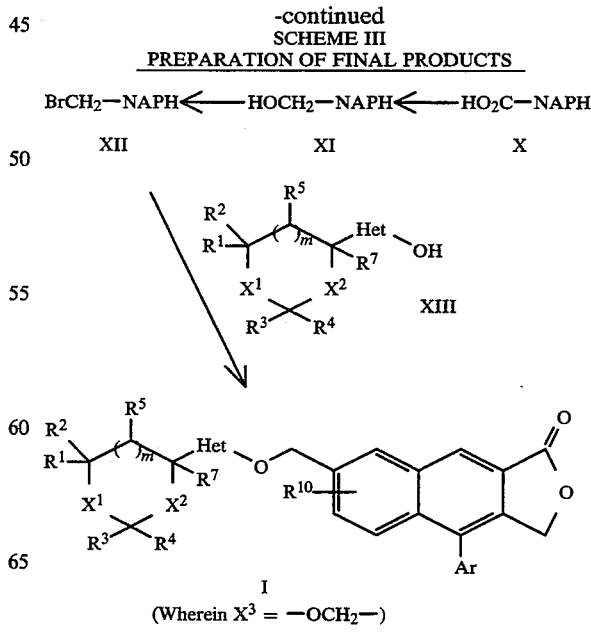

SCHEME IV
PREPARATION OF FINAL PRODUCTS

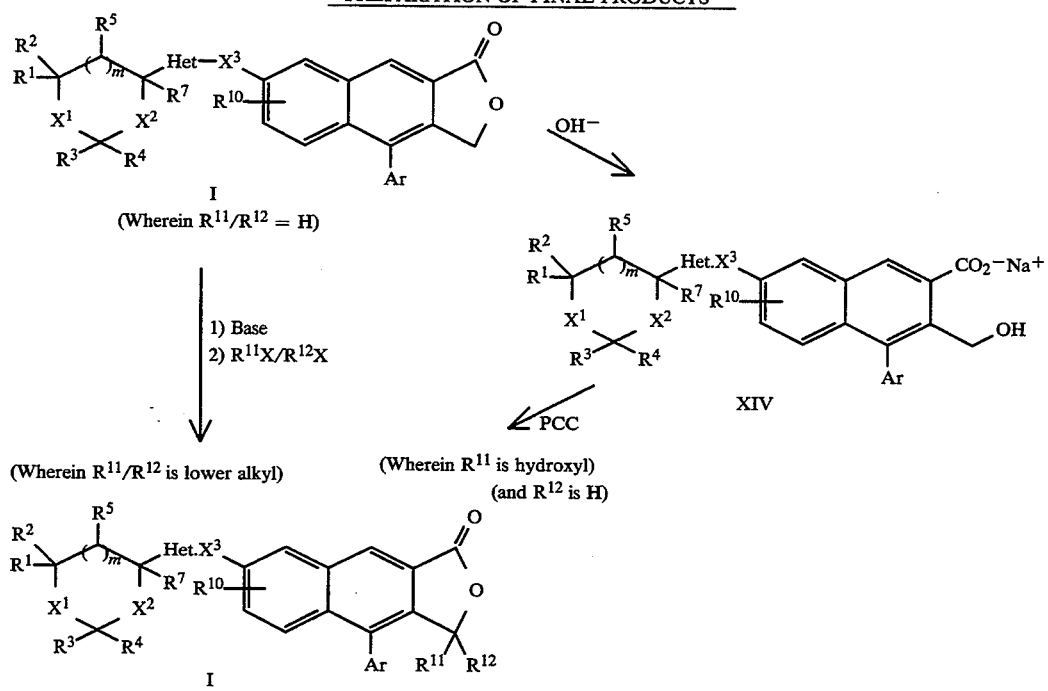

Representative Compounds

Table I illustrates compounds representative of the present invention.

TABLE I

| EX | $R^1$ | $R^3$ | $R^7$ | Het |
|---|---|---|---|---|
| 1 | H | H | OH | 5,3-Pye |
| 2 | H | H | OMe | 5,3-Pye |
| 3 | H | H | OH | 6,2-Pye |
| 4 | H | H | OMe | 6,2-Pye |
| 5 | H | H | OH | 4,2-Pye |
| 6 | H | H | OMe | 4,2-Pye |
| 7 | —CH$_2$O— | | OH | 5,3-Pye |
| 8 | —CH$_2$O— | | OMe | 5,3-Pye |
| 9 | —CH$_2$O— | | OH | 6,2-Pye |
| 10 | —CH$_2$O— | | OMe | 6,2-Pye |
| 11 | —CH$_2$O— | | OH | 2,4-Pye |
| 12 | —CH$_2$O— | | OMe | 2,4-Pye |

Assays for Determining Biological Activity

Compounds of Formula I can be tested using the following assays to determine their mammalian leukotriene biosynthesis inhibiting activity.

Human 5-Lipoxygenase Inhibitor Screen

Objective of the Assay: The objective of the assay is to select agents which specifically inhibit the activity of human 5-lipoxygenase using a 100,000x g supernatant fraction prepared from insect cells infected with recombinant baculovirus containing the coding sequence for human 5-lipoxygenase. Enzyme activity is measured spectrophotometrically from the optimal rate of conjugated diene formation (A$_{234}$) measured after the incubation of the enzyme with arachidonic acid in the presence of ATP, calcium ions and phosphatidylcholine.

Description of Procedure: The activity of 5-lipoxygenase is measured using a spectrophotometric assay and recombinant human 5-lipoxygenase as a source of enzyme. The 100,000x g fraction from S19 cells infected with the recombinant baculovirus rvH5LO(8-1) containing the coding region sequence for human 5-lipoxygenase is prepared as described by Denis et al. (J. Biol. Chem., 266, 5072–5079 (1991)). The enzymatic activity is measured, using a spectrophotometric assay from the optimal rate of conjugated diene formation (A$_{234}$) using the procedure described by Riendeau etal. (Blochem. Pharmacol. 38, 2323–2321, (1989)) with minor modifications. The incubation mixture contains 50 mM sodium phosphate pH 7.4, 0.2 mM ATP, 0.2 mM CaCl$_2$, 20 μM arachidonic acid (5 μL from a 100-fold concentrated solution in ethanol), 12 μg/mL phosphatidylcholine, an aliquot of the 100,000x g fraction (2–10 μL) and inhibitor (0.5 mL final volume). Inhibitors are added as 500-fold concentrated solutions in DMSO. Reactions are initiated by the addition of an aliquot of the enzyme preparation and the rate of conjugated diene formation is followed for 2 minutes at room temperature. The reactions are performed in semi-micro cuvettes (0.7 mL capacity, 10 mm path length and 4 mm internal width) and the absorbance changes are recorded with a Hewlett-Packard diode array spectrophotometer (HP 8452A) connected to the ChemStation using UV/VIS Kinetics Software (Hewlett-Packard). Enzymatic activity is calculated from the optimal rate of the reaction by a linear fit of the variation of A$_{234}$ during the first twenty seconds using the least square method for the equation A$_{234}$=V$_o$t+A$_o$ where V$_o$ is the rate, t is the time, and A$_o$ is the absorbance at zero time. The results are expressed as percentages of inhibition of the reaction rate relative to controls (typically between 0.15–0.21 AU/min) containing the DMSO vehicle.

Rat Peritoneal Polymorphonuclear (PMN) Leukocyte Assay

Rats under ether anesthesia are injected (i.p.) with 8 mL of a suspension of sodium caseinate (6 grams in ca. 50 mL water). After 15–24 hr. the rats are sacrificed ($CO_2$) and the cells from the peritoneal cavity are recovered by lavage with 20 mL of buffer (Eagles MEM containing 30 mM HEPES adjusted to pH 7.4 with NaOH). The cells are pelleted (350x g, 5 min.), resuspended in buffer with vigorous shaking, filtered through lens paper, recentrifuged and finally suspended in buffer at a concentration of 10 cells/mL. A 500 µL aliquot of PMN suspension and test compound are preincubated for 2 minutes at 37° C., followed by the addition of 10 µM calcium ionophore A-23187. The suspension is stirred for an additional 4 minutes then bioassayed for $LTB_4$ content by adding an aliquot to a second 500 µL portion of the PMN at 37° C. The $LTB_4$ produced in the first incubation causes aggregation of the second PMN, which is measured as a change in light transmission. The size of the assay aliquot is chosen to give a submaximal transmission change (usually −70%) for the untreated control. The percentage inhibition of $LTB_4$ formation is calculated from the ratio of transmission change in the sample to the transmission change in the compound-free control.

Human Polymorphouclear (PMN) Leukocyte $LTB_4$ Assay

A. Preparation of Human PMN, Human blood is obtained by antecubital venepuncture from consenting volunteers who have not taken medication within the previous 7 days, The blood is immediately added to 10% (v/v) trisodium citrate (0.13M) or 5% (v/v) sodium heparin (1000 IU/mL). PMNs are isolated from anticoagulated blood by dextran sedimentation of erythrocytes followed by centrifugation through Ficoll-Hypaque (specific gravity 1.077), as described by Boyum (Scand. J. Clin. Lab. Invest., 21 (Supp 97), 77 (1968)). Contaminating erythrocytes are removed by lysis following exposure to ammonium chloride (0.16M) in Tris buffer (pH 7.65), and the PMNs are resuspended at $5 \times 10^5$ cells/mL in HEPES (15 mM)-buffered Hanks balanced salt solution containing $Ca^{2+}$ (1.4 mM) and $Mg^{2+}$ (0.7 mM), pH 7.4.

B. Generation and Radioimmunoassay of $LTB_4$. PMNs (0.5 mL; $2.5 \times 10^5$ cells) are placed in plastic tubes and incubated (37° C., 2 min) with test compounds at the desired concentration or vehicle (DMSO, final concentration 0.2%) as control. The synthesis of $LTB_4$ is initiated by the addition of calcium ionophore A23187 (final concentration 10 µM) or vehicle in control samples and allowed to proceed for 5 minutes at 37° C. The reactions are then terminated by the addition of cold methanol (0.25 mL) and samples of the entire PMN reaction mixture are removed for radioimmunoassay of $LTB_4$.

Samples (50 µL) of authentic $LTB_4$ of known concentration in radioimmunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer are added to reaction tubes. Thereafter [$^3$H]-$LTB_4$ (10 nCi in 100 µL RIA buffer) and $LTB_4$-antiserum (100 µL of a 1:3000 dilution in RIA buffer) are added and the tubes vortexed. Reactants are allowed to equilibrate by incubation overnight at 4° C. To separate antibody-bound from free $LTB_4$, aliquots (50 µL) of activated charcoal (3% activated charcoal in RIA buffer containing 0.25% Dextran T-70) are added, the tubes vortexed, and allowed to stand at room temperature for 10 minutes prior to centrifugation (1500x g; 10 min; 4° C.). The supernatants containing antibody-bound $LTB_4$ are decanted into vials and Aquasol 2 (4 mL) is added. Radioactivity is quantified by liquid scintillation spectrometry. The specificity of the antiserum and the sensitivity of the procedure have been described by Rokach et al., Prostaglandins Leukotrienes and Medicine, 13, 21 (1984). The amount of $LTB_4$ produced in test and control samples is calculated. Inhibitory dose-response curves are constructed using a four-parameter algorithm and from these the $IC_{50}$ values are determined.

Human Whole Blood Assay In Vitro for $LTB_4$ Production

Fresh blood is collected in heparinized tubes by venipuncture from human volunteers. A 500 µL aliquot is incubated with one of the test compounds at final concentrations varying from 3 nM to 3 mM at 37° C. for 15 min. Drug stock solutions are made up in DMSO and 1 µL of the stock solution is added to each assay tube. The blood is then incubated with A23187 (in 5 µL autologous plasma, 25 µM final concentration) at 37° C. for 30 min. At the end of incubation, plasma is obtained (12,000x g, 15 min) and a 100 µL aliquot is added to 400 µL methanol for protein precipitation. The mixture is vortexed, centrifuged and the supernatant stored at −70° C. until assayed for $LTB_4$ by standard RIA.

Asthmatic Rat Assay

Rats are obtained from an inbred line of asthmatic rats. Both female (190–250 g) and male (260–400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate is supplied by Sandoz Ltd., Basel.

The challenge and subsequent respiratory recordings are carried out in a clear plastic box with internal dimensions $10 \times 6 \times 4$ inches. The top of the box is removable; in use, it is held firmly in place by four clamps and an airtight seal is maintained by a soft rubber gasket. Through the center of each end of the chamber a DeVilhiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Buxco Electronics preamplifier (Buxco Electronics Inc., Sharon, Conn.). The preamplifier is connected to a Beckman Type R Dynograph and to a Buxco computer consisting of waveform analyser, Data Acquisition Logger with special software. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 post sensitization. In order to eliminate the serotonin component of the response, rats are pretreated intravenously 5 minutes prior to aerosol challenge with 3.0 pg/kg of methysergide. Rats are then exposed to an aerosol of 3% EA in saline for exactly 1 minute, then their respiratory profiles are recorded for a further 30 minutes. The duration of continuous dyspnea is measured by the Buxco computer.

Compounds are generally administered either orally 2-4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. The activity of compounds is determined in terms of their ability to decrease the duration of antigen-induced dyspnea in comparison with a group of vehicle-treated controls. Usually, a compound is evaluated at a series of doses and an $ED_{50}$ is determined. This is defined as the dose (mg/kg) which would inhibit the duration of symptoms by 50%.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1%. methocel solution (methylcellulose, 65HG, 400 cps) and given in a volume of 1 mL/kg body weight. For aerosol administration of compounds, a DeVilbiss ultrasonic nebulizer is utilized. Pretreatment periods vary from 5 minutes to 4 hours before the monkeys are challenged with aerosol doses of either leukotriene $D_4$ ($LTD_4$) or *Ascaris suum* antigen, 1:25 dilution.

Following challenge, each minute of data is calculated by computer as a percent change from control values for each respiratory parameter including airway resistance ($R_L$) and dynamic compliance ($C_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used. (References: McFarlane, C. S. et al. , Prostaglandins, 28, 173–182 (1984) and McFarlane, C. S. et al., Agents Actions, 22, 63–68 (1987).)

Prevention of Induced Bronchoconstriction in Allergic Sheep

A. Rationale

Certain allergic sheep with known sensitivity to a specific antigen (*Ascaris suum*) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods. Animal Preparation

Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greer Diagnostics, Lenois, N.C.) and b) they have previously responded to inhalation challenge with *Ascaris suum* with both an acute bronchoconstriction and a late bronchial obstruction (W. M. Abraham, et al., Am. Rev. Resp. Dis., 128, 839–44 (1983)).

Measurement of Airway Mechanics

The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one mL of air), which is positioned such that inspiration produces a negative pressure deflection with clearly discernible cardiogenic oscillations. Lateral pressure in the trachea is measured with a sidehole catheter (inner dimension, 2.5 mm) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). For the measurement of pulmonary resistance ($R_L$), the maximal end of the nasotrachel tube is connected to a pneumotachograph (Fleisch, Dyna Sciences, Blue Bell, Pa.). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems

Aerosols of *Ascaris suum* extract (1:20) are generated using a disposable medical nebulizer (Raindrop ®, Puritan Bennett), which produces an aerosol with a mass median aerodynamic diameter of 6.2 $\mu M$ (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is connected to the inspiratory part of a Harvard respirator. The aerosol is delivered at a tidal volume of 500 mL of a rate of 20 per minute. Thus, each sheep receives an equivalent dose of antigen in both placebo and drug trials.

Experimental Protocol

Prior to antigen challenge baseline measurements of $SR_L$ are obtained, infusion of the test compound is started 1 hr prior to challenge, the measurement of $SR_L$ repeated and then the sheep undergoes inhalation challenge with *Ascaris suum* antigen. Measurements of $SR_L$ are obtained immediately after antigen challenge and at 1, 2, 3, 4, 5, 6, 6.5, 7, 7.5, and 8 hrs after antigen challange. Placebo and drug tests are separated by at least 14 days. In a further study, sheep are given a bolus dose of the test compound followed by an infusion of the test compound for 0.5–1 hr prior to Ascaris challenge and for 8 hrs after Ascaris as described above.

Statistical Analysis

A Kruskal-Wallis one way ANOVA test is used to compare the acute immediate responses to antigen and the peak late response in the controls and the drug-treated animals,

PREPARATION OF ALCOHOLS

Alcohol 1:
5-[4-(4-Hydroxy)tetrahydropyranyl]-pyridin-3-ylmethanol

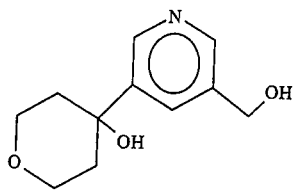

Step 1:
5-Bromo-O-tert-butyldiphenylsilylpyridin-3-ylmethanol

To a solution of 5-bromopyridin-3-ylmethanol (Chem. Pharmo Bull. 1990, 38, 2446) (29 g, 154 mmoL) and tert-butylchlorodiphenylsilane (47.5 g, 173 mmoL) in $CH_2Cl_2$ (500 mL) at r.t., there was added imidazole (15.8 g, 232 mmoL). The mixture was stirred for 1 hr. and filtered. The filtrate was evaporated and the residue chromatographed on silica gel eluting with a 1:7 mixture of EtOAc and hexane, to afford the product as a colorless oil.

Step 2:
5-[4-(4-Hydroxy)tetrahydropyranyl]-O-tert-butyldiphenylSilylpyridin-3-ylmethanol To a solution of the silylether from Step 1 (50 g, 117 mmoL) in THF (500 mL), cooled to −70° C., there was slowly added n-BuLi 1.12M in hexanes (115 mL, 129 mmoL) affording a dark brown solution. To this, there was added a solution of tetrahydro-4H-pyran-4-one (14.1 g, 141 mmoL) in THF (925 mL). The resulting mixture was stirred for 1 hr. at −70° C., then quenched slowly with saturated aqueous $NH_4Cl$ (50 mL) and allowed to warm up to r.t. After diluting with EtOAc (500 mL) the mixture was washed (4×) with brine, dried over $Na_2SO_4$, and evaporated. Chromatography on silica gel, eluting with EtOAc, afforded the product as an oil which solidified.

Step 3:
5-[4-(4-Hydroxy)tetrahydropyranyl]pyridin-3-ylmethanol

To a solution of the silylether from Step 2 (20.35 g, 45.5 mmoL) in THF (350 mL), there was added $Bu_4NF$ 1M in THF (52 mL) and the mixture was stirred at r.t. for 1 hr. The solvent was evaporated and the residue chromatographed as a short column of silica gel, eluting with a 1:4 mixture of EtOH and EtOAc to afford the title product which was obtained, after trituration with $Et_2O$ and filtration, as a light yellow solid; m.p. 145°–147° C.

Alcohol 2:
6-[4-(4-Hydroxy)tetrahydropyranyl]-pyridin-2-ylmethanol

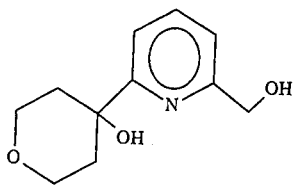

Step 1:
2-Bromo-6-[4-(4-hydroxy)tetrahydropyranyl]-pyridine

A solution of 2,6-dibromopyridine (15 g) in $Et_2O$ (375 mL) was cooled to −78° C. To the resulting suspension was slowly added n-BuLi 2M in hexanes (47.5 mL, 0.9 eq.) and the resulting mixture was stirred for a further 15 min. at −78° C. There was slowly added a solution of tetrahydro-4H-pyran-4-one (11.6 g) in $Et_2O$ (25 mL). The resulting white suspension was stirred at −78° C. for an additional 15 min. There was added saturated aqueous $NH_4Cl$ (100 mL) and the mixture was allowed to warm up to r.t. After dilution with EtOAc, the organic phase was washed (4x) with brine, dried, and evaporated. The residue was triturated with $Et_2O$ and filtered to afford the title product as a white solid; m.p. 131°–133° C.

Step 2:
6-[4-(4-hydroxy)tetrahydropyranyl]pyridin-2-ylmethanol

To a solution of the bromo derivative from Step 1 (7.7 g) in THF (50 mL) and $Et_2O$ (150 mL), cooled to 0° C., there was slowly added n-BuLi 2M in hexanes (30 mL) affording a red-brown suspension. An inlet tube above the surface of the mixture was connected to a flask in which paraformaldehyde (25 g) was gently heated at 175° C. to generate formaldehyde. When all the paraformaldehyde had been decomposed, to the reaction mixture was added saturated aqueous $NH_4Cl$ (100 mL) and EtOAc (500 mL). The organic phase was washed (4×) with brine, dried, and evaporated to a residue which was chromatographed on silica gel, eluting with EtOAc to afford the title product as a thick yellow oil.

Alcohol 3:
6-[4-(4-Methoxy)tetrahydropyranyl]-pyridin-2-ylmethanol

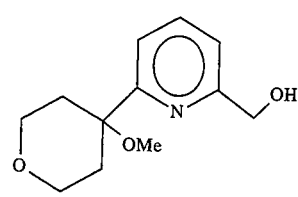

Step 1:
2-Bromo-6-[4-(4-methoxy)tetrahydropyranyl]-pyridine

To a suspension of KH (35% dispersion in oil, 1.25 g) in THF (75 mL), cooled to 0° C., there was added 2-bromo-6-[4-(4-hydroxy)tetrahydropyranyl]-pyridine from Alcohol 2, Step 1. When gassing had subsided, the mixture was warmed to r.t. and a thick suspension resulted. To this was added methyl iodide (1.71 g) and the resulting suspension was stirred at r.t. for 30 min. The THF was evaporated away, and the residue was partitioned between H₂O and EtOAc. The residue from evaporation of the organic phase was triturated with hexane and filtered to afford the product as a white solid; m.p. 69°–71° C.

Step 2:
6-[4-(4-Methoxy)tetrahydropyranyl]pyridin-2-ylmethanol

Following the procedure described in Alcohol 2, Step 2, but substituting the bromo derivative from Step 1 for 2-bromo-6-[4-(4-hydroxy)tetrahydropyranyl]pyridine, the title product was obtained as a white solid; m.p. 84°–86° C.

Alcohol 4:
4-[4-(4-Hydroxy)tetrahydropyranyl]-pyridin-2-ylmethanol

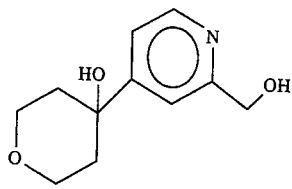

Following the procedure described in Alcohol 1, Steps 1–3, but substituting 4-bromopyridin-2-ylmethanol (Chem. Pharm. Bull. 1990, 38, 2446) for 5-bromo-pyridin-3-ylmethanol as starting material, the title product was obtained as a white solid.

Alcohol 5: (1S,5R)
5-[3-(3α-Hydroxy-6,8-dioxabicyclo[3.2.1]octanyl)]pyridin-3-yl-methanol

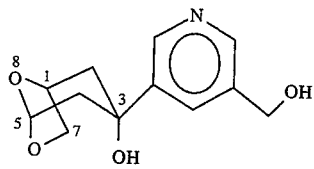

Step 1:
2,4-Di-O-p-toluenesulfonyl-1,6-anhydro-β-D-glucose

A solution of 1,6-anhydro-β-D-glucose (50 g, 308 mmoL) in dry pyridine (100 mL) at 0° C. was added dropwise a solution of p-toluenesulfonyl chloride (123 g, 647 mmoL) dissolved in CHCl₃ (350 mL) and pyridine (200 mL). The reaction mixture was stirred at r.t. for at least 2 days. Water was added and the reaction mixture was stirred for ~1 hr, then the organic layer was decanted and the aqueous phase was reextracted with CHCl₃. The combined organic layers were washed with H₂SO₄ (10%) until the pH remains acidic, then finally washed with a saturated NH₄OAc solution. The resulting organic layer was dried over MgSO₄ and the solvent evaporated. The syrup obtained was flash chromatographed on silica gel eluting with hexane:EtOAc (1:1) to give the title compound an oil.

Step 2: (1S,3S,5R) 6,8-Dioxabicyclo[3.2.1]octan-3-ol

The ditosylate derivative from Step 1 (107 g, 0.228 mmoL) was dissolved in THF (1.6 L) at −40° C. and Super-hydride in THF (800 mL, 1M, 0.8 mmoL) was slowly added. The resulting reaction mixture was stirred at r.t. overnight. The reaction was cannulated into cold H₂O (226 mL) using external cooling, then NaOH 3N (640 mL, 1.92 mmol) and H₂O₂ (30%) (490 mL, 4.3 mmol) were successively added. The reaction was stirred at r.t. for 1 hr, then the supernatant (THF layer) was separated from the aqueous layer and concentrated. The resulting residue was combined with the aqueous layer and extracted with CH₂Cl₂ using a continuous extractor. The organic layer was dried (MgSO₄) and evaporated to dryness. The oily residue was dissolved in hot Et₂O, filtered, and evaporated to dryness affording the title compound contaminated with the 2-octanol isomer. The crude product was used as such for the next step.

Step 3: (1S,5R) 6,8-dioxabicyclo[3.2.1]octan-3-one

The crude alcohol from Step 2 (16.6 g, 89 mmoL) in CH₂Cl₂ (200 mL) was added slowly to a suspension of PCC (38.4 g, 178 mmoL) and celite (22 g) in CH₂Cl₂ (400 mL) and stirred for 1 hr. The reaction mixture was diluted with Et₂O (600 mL) and filtered over celite. The filtrate was evaporated and the residue distilled with a Kügelrohr apparatus (100° C., 1.8 mm/Hg) affording the title product as an oil.

Step 4: (1S,5R)
5-[3-(3α-Hydroxy-6,8-dioxabicyclo[3.2.1]octanyl)]pyridin-3-ylmethanol Following the procedure described in Alcohol 1, Steps 2–3, but substituting (1S,5R) 6,8-dioxabicyclo[3.2.1]octan-4-one from Step 3, for tetrahydro-4H-pyran-4-one, the title product was obtained as a white solid.

Alcohol 6: (1S,5R)
6-[3-(3α-Hydroxy-6,8-dioxabicyclo[3.2.1]octanyl)]pyridin-2-yl-methanol

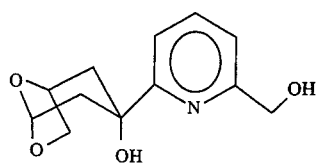

Step 1:
6-Bromo-O-tert-butyldiphenylsilylpyridin-2-ylmethanol

Following the procedure described in Alcohol 1, Step 1, but substituting 6-bromopyridin-2-ylmethanol (Chem. Pharm. Bull. 1990, 38, 2446) for 5-bromopyridin-3-ylmethanol, the title product was obtained as a colorless oil.

Step 2: (1S,5R) 6-[3-(3α-Hydroxy-6,8-dioxabicyclo-[3.2.1]octanyl)-]pyridin-2-ylmethanol Following the procedure described in Alcohol 1, Steps 2-3, but substituting 6-bromo-O-tert-butyldiphenylsilylpyridin-2-ylmethanol from Step 1, for 5-bromo-O-tert-butyldiphenylsilylpyridin-3-ylmethanol and substituting (1S,5R) 6,8-dioxabicyclo[3.2.1]-octan-4-one from Alcohol 5, Step 3, for tetrahydro-4H-pyran-4-one, the title product was obtained as a white solid.

The invention is further defined by reference to the following examples, which are intended to be illustrative and not limiting. All temperatures are in degrees Celsius.

EXAMPLE 1

3-Hydroxymethyl-4-phenyl-7-[5-[4-(4-hydroxy)tetrahydropyranyl]pyridin-3-ylmethoxy]-2-naphthoic acid, lactone form

Step 1: Benzaldehyde phenyl dithioacetal

To a solution of benzaldehyde (13.3 g) and thiophenol (26 mL) in isopropyl acetate (200 mL), cooled in an ice-water bath, there was slowly added $BF_3.Et_2O$ (15 mL). The resulting mixture was stirred in the cold for an additional hour. There was slowly added 10% aqueous $K_2CO_3$ (100 mL). The phases were separated, the aqueous phase was extracted with EtOAc. The combined organic fractions were then washed with $H_2O$ (3×), dried, and evaporated to an oil which was used as such.

Step 2: 3-[Phenyl-bis(phenylthio)methyl]-2-(3-benzyl-oxy-α-hydroxybenzyl)butyrolactone To a solution of the dithioacetal from Step 1 (5.7 g) in THF (100 mL), at −70° C. there was slowly added 2.1M n-BuLi in hexanes (9.0 mL). The resulting dark solution was stirred for a further 20 min. at −70° C., then there was added dropwise 2-(5H)furanone (Omega Inc. 1.6 mL), and 30 min. later, a solution of 3-benzyloxybenzaldehyde (Aldrich, 2.0 g) in THF (20 mL). The mixture was stirred a further hour at −70° C., then there was slowly added glacial HOAc (1.5 mL). The mixture was allowed to warm up to r.t., diluted with $Et_2O$ (500 mL), washed with brine (4×), dried, and evaporated. The residue was used as such in the next step.

Step 3: 3-Hydroxymethyl-4-phenyl-7-hydroxy-2-naphthoic acid, lactone form

The crude product from Step 2 was dissolved in thioanisole (20 mL), there was added TFA (30 mL), and the mixture was stirred at r.t. for 18 hr. After cooling, the TFA was evaporated, the residue was diluted with $Et_2O$ (100 mL) and after 20 min., the insoluble solid was filtered to afford the desired title compound.

Step 4: 3-Hydroxymethyl-4-phenyl-7-[5-[4-(4-hydroxy)-tetrahydropyranyl]pyridin-3-ylmethoxy]-2-naphtoic acid, lactone form To a mixture of lactone (238 mg) from Step 3, 5-[4-(4-hydroxy)tetrahydropyranyl]pyridin-3-yl-methanol (Alcohol 1, 180 mg) and triphenylphosphine (270 mg) in THF (8 mL), there was added di-tert-butyl azodicarboxylate (179 mg) and the mixture was stirred at r.t. for 2 hr. After evaporation of the THF, the residue was chromatographed on a column of silica gel, eluting with a 1:9 mixture of EtOH and EtOAc. The product obtained was triturated with a 1:1 mixture of $Et_2O$ and hexane, affording on filtration the title compound as a cream-colored solid; m.p. 172°–174° C.

EXAMPLES 2-12

Following the procedure described in Example 1, Step 4, but substituting the appropriate alcohol for 5-[4-(4-hydroxy)tetrahydropyranyl]pyridin-3-yl-methanol the compounds of Examples 2-12 are obtained.

What is claimed is:

1. A compound of the formula:

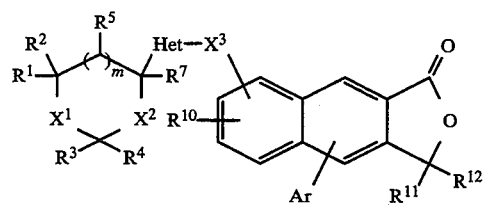

wherein:
$R^1, R^5$, and $R^{11}$ is each independently H, OH, lower alkyl, or lower alkoxy;
$R^2$ is H, lower alkyl, or together with $R^1$ forms a double bonded oxygen (=O);
$R^3$ is H, lower alkyl, hydroxy lower alkyl, lower alkoxy lower alkyl, or is joined to $R^1$ to form a carbon bridge of 2 or 3 carbon atoms or a monooxa carbon bridge of 1 or 2 carbon atoms, said bridge optionally containing a double bond;
$R^4$, $R^{12}$, and $R^{14}$ is each independently H or lower alkyl;
$R^6$ is H or lower alkyl, or two $R^6$ groups on the same or adjacent carbons can form a saturated ring of 3 to 8 members;
$R^7$ is H, OH, lower alkyl, lower alkoxy, lower alkylthio, or lower alkylcarbonyloxy;
$R^8$ is H, halogen, lower alkyl, lower alkoxy, $CF_3$, CN, $COR^{14}$, or a non-bonded electron pair;
$R^9$ and $R^{10}$ is each independently H, lower alkyl, lower alkoxy, hydroxy lower alkyl, lower alkoxy lower alkyl, lower alkylthio lower alkyl, lower alkylthio lower alkylcarbonyl, $(R^8)$2-phenylthio lower alkyl, halogen, CN, $NO_2$, $CF_3$, $N_3$, $N(R^{13})_2$, $NR^{13}COR^{14}$, $NR^{13}CON(R^{13})_2$, $SR^{15}$, $S(O)R^{15}$, $S(O)_2R^{15}$, $S(O)_2N(R^{13})_2$, $COR^{14}$, $CON(R^{13})_2$, $CO_2R^{14}$, $C(R^{14})_2OC(R^{14})_2$-$CO_2R^{14}$, or $C(R^{14})_2CN$;
$R^{10}$ is attached to either ring of the naphthalene ring system; $R^{13}$ is H, or lower alkyl, or two $R^{13}$ groups attached to the same nitrogen may form a saturated ring of 5 or 6 members, optionally containing a second heteroatom chosen from O, S or $NR^4$;
$R^{15}$ is lower alkyl, phenyl-$(R^8)_2$, or $CF_3$;
$X^1$ is O;
$X^2$ is $C(R^6)_2$;
$X^3$ is $C(R^6)_2O$;
Ar is phenyl$(R^9)_2$;
Het is pyridyl-$(R^8)_2$ and
m is 1;
or a pharmaceutically acceptable salt thereof.

2. A compound of claim 1 of the formula:

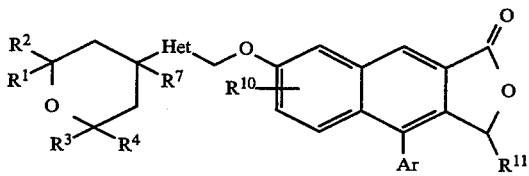

or a pharmaceutically acceptable salt thereof.

3. A compound of claim 1 of the formula:

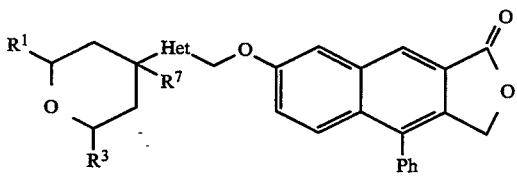

wherein:

R$^1$ is H, Me, or OMe;
R$^3$ is H or Me;
R$^1$ and R$^3$ together are —CH=CH—, —CH$_2$CH$_2$—, —OCH$_2$—, or —CH$_2$O—;
R$^7$ is OH or OMe; and
Het is 5,3-Pye; 6,2-Pye; 4,2-Pye; or 2,4-Pye;
or a pharmaceutically acceptable salt thereof.

4. A compound of claim 3 of the formula:

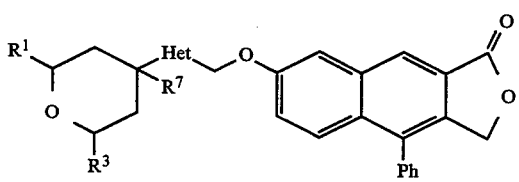

wherein the substituents are as follows:

| EX | R$^1$ | R$^3$ | R$^7$ | Het |
|---|---|---|---|---|
| 1 | H | H | OH | 5,3-Pye |
| 2 | H | H | OMe | 5,3-Pye |
| 3 | H | H | OH | 6,2-Pye |
| 4 | H | H | OMe | 6,2-Pye |
| 5 | H | H | OH | 4,2-Pye |

| EX | R$^1$ | R$^3$ | R$^7$ | Het |
|---|---|---|---|---|
| 6 | H | H | OMe | 4,2-Pye |
| 7 | —CH$_2$O— | | OH | 5,3-Pye |
| 8 | —CH$_2$O— | | OMe | 5,3-Pye |
| 9 | —CH$_2$O— | | OH | 6,2-Pye |
| 10 | —CH$_2$O— | | OMe | 6,2-Pye |
| 11 | —CH$_2$O— | | OH | 2,4-Pye |
| 12 | —CH$_2$O— | | OMe | 2,4-Pye |

5. A pharmaceutical composition comprising a therapeutically effective amount of a compound of claim 1 and a pharmaceutically acceptable carrier.

6. A pharmaceutical composition of claim 5 additionally comprising an effective amount of a second active ingredient selected from the group consisting of non-steriodal anti-inflammatory drugs; peripheral analgesic agents; cyclooxygenase inhibitors; leukotriene antagonists; leukotriene biosynthesis inhibitors; H$_1$- or H$_2$-receptor antagonists; antihistaminic agents; prostaglandin antagonists; thromboxane antagonists; thromboxane synthetase inhibitors; and ACE antagonists.

7. A pharmaceutical composition of claim 6, wherein the second active ingredient is a non-steriodal anti-inflammatory drug.

8. A pharmaceutical composition comprising a therapeutically effective amount of a compound of claim 1, an effective amount of a second active ingredient which is a non-steriodal anti-inflammatory drug, and a pharmaceutically acceptable carrier, wherein the weight ratio of said compound of claim 1 to said second active ingredient ranges from about 1000:1 to 1:1000.

9. A method of preventing the synthesis, the action, or the release of SRS-A (slow reacting substance of anaphyloris) or leukotrienes in a mammal which comprises administering to said mammal an effective amount of a compound of claim 1.

10. A method of claim 9 wherein the mammal is man.

11. A method of treating asthma in a mammal comprising administering to a mammal in need of such treatment a therapeutically effective amount of a compound of claim 1.

12. A method of treating inflammatory diseases of the eye in a mammal which comprises administering to a mammal in need of such treatment a therapeutically effective amount of a compound of claim 1.

13. The method of claim 12 wherein the mammal is man.

* * * * *